US00PP27402P2

(12) United States Plant Patent
Ronald

(10) Patent No.: US PP27,402 P2
(45) Date of Patent: Nov. 22, 2016

(54) ***CORNUS* PLANT NAMED 'JEFREB'**

(50) Latin Name: *Cornus alba*
Varietal Denomination: Jefreb

(71) Applicant: Jeffries Nurseries Ltd, Portage la Prairie (CA)

(72) Inventor: Wilbert Ronald, Portage la Prairie (CA)

(73) Assignee: JEFFRIES NURSERIES, LTD, Portage la Prairie, Manitoba (CA)

( * ) Notice: Subject to any disclaimer, the term of this patent is extended or adjusted under 35 U.S.C. 154(b) by 60 days.

(21) Appl. No.: 14/121,603

(22) Filed: Sep. 23, 2014

(51) Int. Cl.
*A01H 5/00* (2006.01)

(52) U.S. Cl.
USPC ..... Plt./220

(58) Field of Classification Search
USPC ..... Plt./220
See application file for complete search history.

(56) References Cited

PUBLICATIONS

PLUTO Plant Variety Database Feb. 19, 2016. p. 1.*

* cited by examiner

*Primary Examiner* — Annette Para
(74) *Attorney, Agent, or Firm* — Penny J. Aguirre

(57) ABSTRACT

A new cultivar of *Cornus*, 'Jefreb', that is characterized by its compact plant habit that is broader than it is tall, its stems that are narrow in diameter and densely branched, and red in color during the winter, and its foliage that is green in color.

2 Drawing Sheets

Botanical classification: *Cornus alba.*
Variety denomination: 'Jefreb'.

BACKGROUND OF THE INVENTION

The present invention relates to a new and distinct cultivar of *Cornus*, botanically known as *Cornus alba* 'Jefreb' and will be referred to hereafter by its cultivar name, 'Jefreb'. 'Jefreb' is a new cultivar of red twig dogwood, a shrub grown for use as an ornamental landscape plant.

The Inventor discovered the new cultivar as naturally occurring branch mutation of the cultivar 'Bailhalo' (U.S. Plant Pat. No. 8,722) in his trial garden in Portage la Prairie, Manitoba, Canada, in spring 2005.

Asexual propagation of the new cultivar was first accomplished by the Inventor using stem cuttings in summer of 2006 in Portage la Prairie, Manitoba, Canada. Asexual propagation of the new cultivar by stem cuttings has been determined that the characteristics are stable and are reproduced true to type in successive generations.

SUMMARY OF THE INVENTION

The following traits have been repeatedly observed and represent the characteristics of the new cultivar. These attributes in combination distinguish 'Jefreb' as unique cultivar of *Cornus*.

1. 'Jefreb' exhibits a compact plant habit that is broader than it is tall.
2. 'Jefreb' exhibits stems that are narrow in diameter and densely branched.
3. 'Jefreb' exhibits stems that are red in color during the winter.
4. 'Jefreb' exhibits foliage that is medium green in color.

The parent plant of 'Jefreb', 'Bailhalo', differs from 'Jefreb' in having variegated foliage, in having stems that are medium in diameter and moderately branched, and in being nearly the same height and width. 'Jefreb' can be most closely compared to the *Cornus* cultivars 'Minbat' (not patented) and 'Cream Cracker' (U.S. Plant Pat. No. 12,830). 'Minbat' is similar to 'Jefreb' in having a compact growth habit and in having red stems in the winter. 'Minbat' differs from 'Jefreb' in having a more upright, rounded plant form and in having stems that are less densely branched. 'Cream Cracker' differs from 'Jefreb' in having variegated foliage that is gray-green in color with creamy white colored margins, and in being taller in height and wider in diameter.

BRIEF DESCRIPTION OF THE DRAWINGS

The accompanying colored photographs illustrate the overall appearance and distinct characteristics of the new *Cornus.*

The photograph of the plants in FIG. 1 was taken of five year-old plants of 'Jefreb' as field grown outdoors in Portage la Prairie, Manitoba, Canada and provides a view of the overall plant habit of 'Jefreb'.

Figure 1:
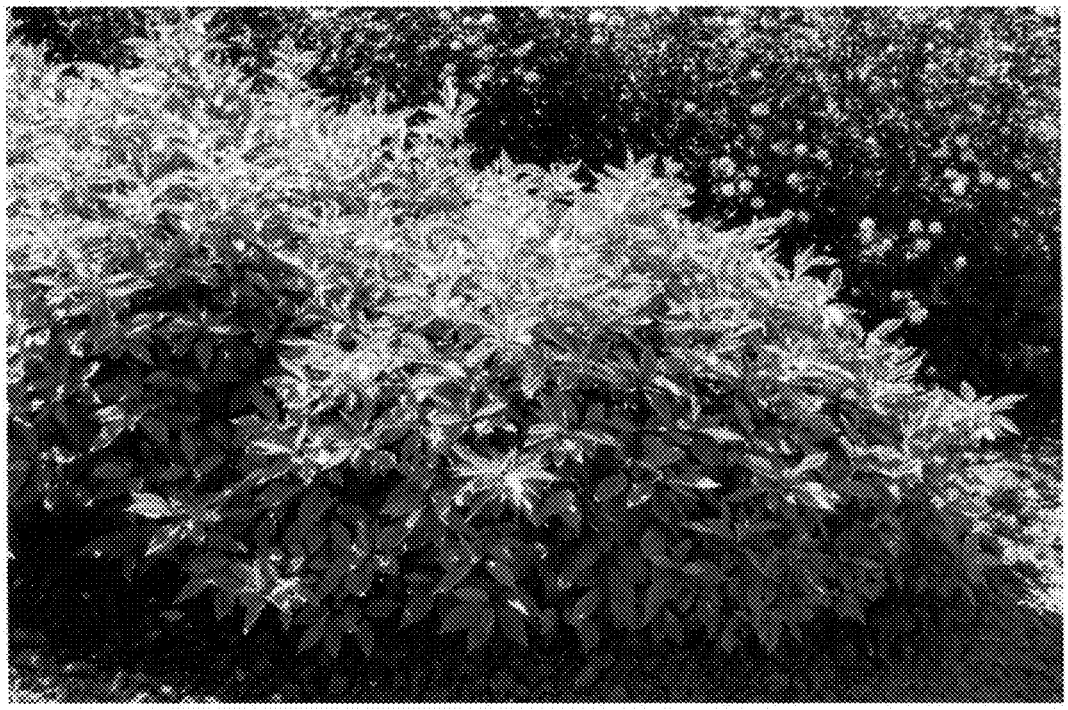
Figure 2:
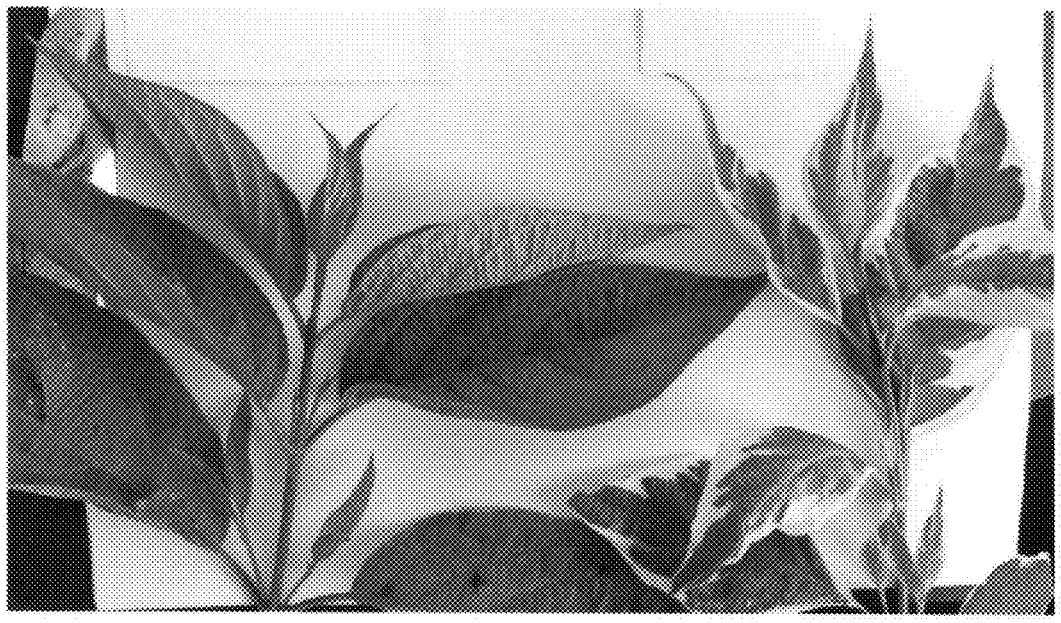

The photograph of the plants in FIG. 2 was taken of three year-old plants of 'Jefreb' as grown outdoors in 9-liter containers in Portage la Prairie, Manitoba, Canada and provides a comparison of the foliage of 'Jefreb' on the left and its parent plant, 'Bailhalo' on the right.

The colors in the photographs may differ slightly from the color values cited in the detailed botanical description, which accurately describe the colors of the new *Cornus.*

DETAILED BOTANICAL DESCRIPTION

The following is a detailed description of three year-old plants the new *Cornus* as grown outside in 2-gallon containers in St. Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Deciduous shrub.

*Plant habit.*—Oblate shaped, compact, low, broad, and bushy.

*Plant height and spread.*—Reaches an average of 60 cm in height and 1 m in spread.

*Diseases and pests.*—No unique susceptibility or resistance to diseases or pests have been observed.

*Cold hardiness.*—At least in U.S.D.A. Zone 2.

*Root description.*—Fibrous.

*Propagation*—Stem cuttings.

*Growth rate.*—Moderate to vigorous.

Stem description:

*Shape.*—Oval.

*Stem color.*—New growth; 146B, mature; 146B and suffused with 175A, late summer and fall 183A, winter 185A.

*Stem size.*—Main branches; an average of 1 cm in diameter measured 5 cm above the soil level and 60 cm in length, lateral branches; average of 3 mm in diameter and 35 cm in length.

*Stem surface.*—New growth and mature stems; glabrous, moderately lenticellate, and moderately glaucous, mature; smooth with raised lenticels about 1.5 mm in length and the same color as the stem.

*Branch internode length.*—6 cm.

*Branching.*—Densely branched, average of 4 basal stems, with 10 lateral branches per basal stem.

Foliage description:

*Leaf shape.*—Lanceolate-narrow elliptic.

*Leaf division.*—Simple.

*Leaf base.*—Broadly cuneate.

*Leaf apex.*—Acuminate.

*Leaf fragrance.*—None.

*Leaf venation.*—Pinnate, not conspicuous, color primarily matches leaf coloration on upper surface (with 183A near petiole) and 146D on lower surface.

*Leaf margins.*—Entire.

*Leaf arrangement.*—Opposite.

*Leaf attachment.*—Petiolate.

*Leaf surface.*—Glabrous on upper surface and lower surface.

*Leaf size.*—An average of 10.76 cm in length and 4.96 cm in width.

*Leaf internode length.*—Average of 4.5 cm.

*Leaf color.*—Newly expanded leaves and mature leaves upper surface; 137B, newly expanded leaves and mature leaves lower surface; 191A, fall color upper and lower surface; a blend of 183A and 162A.

*Petioles.*—An average of 2 cm in length and 2 mm in width, 183B in color on sun exposed upper surface and 146D on lower surface, glabrous surface.

*Stipules.*—None.

Flower description: Plants of the new cultivar have not been observed to flower to date.

It is claimed:

1. A new and distinct cultivar of *Cornus* plant named 'Jefreb' as herein illustrated and described.

* * * * *